(12) United States Patent
Madison et al.

(10) Patent No.: US 10,260,865 B1
(45) Date of Patent: Apr. 16, 2019

(54) HIGH RESOLUTION, NON-CONTACT REMOVAL RATE MODULE FOR SERIAL SECTIONING

(71) Applicant: National Technology & Engineering Solutions of Sandia, LLC, Albuquerque, NM (US)

(72) Inventors: Jonathan D. Madison, Albuquerque, NM (US); Elizabeth M. Huffman, Cedar Crest, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/705,178

(22) Filed: Sep. 14, 2017

Related U.S. Application Data

(60) Provisional application No. 62/393,950, filed on Sep. 13, 2016.

(51) Int. Cl.
   *G01B 11/22* (2006.01)
(52) U.S. Cl.
   CPC .................... *G01B 11/22* (2013.01)
(58) Field of Classification Search
   CPC .. G01B 11/22; G01B 11/0675; G01B 11/0683
   See application file for complete search history.

(56) References Cited

U.S. PATENT DOCUMENTS

| | | | |
|---|---|---|---|
| 7,317,964 B1* | 1/2008 | Spowart | G01N 1/06 700/118 |
| 7,319,914 B1 | 1/2008 | Spowart et al. | |
| 7,319,915 B1 | 1/2008 | Spowart et al. | |
| 7,319,916 B1 | 1/2008 | Spowart et al. | |
| 9,062,964 B1* | 6/2015 | Arabi | G01B 11/0691 |
| 2005/0029228 A1* | 2/2005 | Nozawa | G01B 11/0675 216/60 |
| 2005/0157308 A1* | 7/2005 | Brunfeld | G01B 11/0675 356/504 |
| 2010/0015889 A1* | 1/2010 | Shimizu | B24B 37/013 451/5 |
| 2010/0073689 A1* | 3/2010 | Schmitt | G01B 11/0691 356/630 |

(Continued)

OTHER PUBLICATIONS

Adachi Y et al., "Development of fully automated serial-sectioning 3D microscope and topological approach to pearlite and dual-phase microstructure in steels," in: De Graef M, Poulsen HF, Lewis AC, Simmons JP, Spanos G (eds.), *1st International Conference on 3D Materials Science*, held on Jul. 8-12, 2012 in Seven Springs, PA, John Wiley & Sons, Inc., Hoboken, NJ, 2016, pp. 37-42.

(Continued)

*Primary Examiner* — Shawn Decenzo
(74) *Attorney, Agent, or Firm* — Helen S. Baca

(57) ABSTRACT

The present invention relates to a metallographic system including a measurement module configured to provide precise differential measurements of a sample after serial sectioning, as well as methods of employing such a module. In particular example, the measurement module provides differential measurement(s) without contacting the surface of a sample, thereby minimizing contamination of the sample surface.

23 Claims, 11 Drawing Sheets

(56) References Cited

U.S. PATENT DOCUMENTS

| | | | | |
|---|---|---|---|---|
| 2012/0257213 A1* | 10/2012 | Schonleber | ............ | G01B 11/22 |
| | | | | 356/485 |
| 2014/0130613 A1* | 5/2014 | Adiga | ............... | G01N 1/06 |
| | | | | 73/863.01 |
| 2014/0368830 A1* | 12/2014 | Michelt | ............ | G01B 11/0608 |
| | | | | 356/485 |
| 2015/0000345 A1* | 1/2015 | Jiao | ............ | C03B 18/02 |
| | | | | 65/158 |
| 2015/0276381 A1* | 10/2015 | Tayebati | ............ | G01B 11/0608 |
| | | | | 356/496 |
| 2016/0153769 A1* | 6/2016 | Pareschi | ............ | G01B 9/02025 |
| | | | | 356/503 |
| 2017/0249727 A1* | 8/2017 | Mayumi | ............ | G06T 7/74 |
| 2017/0343337 A1* | 11/2017 | Muller | ............ | G01B 11/24 |

OTHER PUBLICATIONS

Alkemper J et al., "Quantitative serial sectioning analysis," *J. Microsc.* 2001;201(3):388-94.

Alkemper J et al., "Three-dimensional characterization of dendritic microstructures," *Acta Materialia* 2001;49(5):897-902.

Brake MRW et al., "Designing energy dissipation properties via thermal spray coatings," *Surf. Coat. Technol.* 2017;310:70-8.

Caron RN et al., "The tempering of Fe—C lath martensite," *Metall. Trans.* 1972;3:2381-9.

Hull DA et al., "Titanium prior-beta grain vol. distribution by quantitative serial sectioning techniques," *Mater. Character.* 1991;26(2):63-71.

Keyence Corp., "High Precision Measurement General Catalog," 2014, Brochure No. MeasurementE-KA-GC3-US, 70 pp.

Kral MV et al., "Three-dimensional analysis and classification of grain-boundary-nucleated proeutectoid ferrite precipitates," *Metall. Mater. Trans. A* 2005;36A(5):1199-207.

Kral MV et al., "Three-dimensional analysis of microstructures," *Mater. Character.* 2000;45(1):17-23.

Kral MV et al., "Three-dimensional analysis of proeutectoid cementite precipitates," *Acta Materialia* 1999;47(2):711-24.

Kral MV et al., "Three-dimensional morphology of cementite precipitates," *Scripta Materialia* 1997;36(8):875-82.

Lund AC et al., "The effects of elastic stress on microstructural development: the three-dimensional microstructure of a γ-γ' alloy," *Acta Materialia* 2002;50(10):2585-98.

Madison JD et al., "3D RoboMET™ characterization," *Sandia Report No. SAND2015-8957R*, 2015, 16 pp.

Madison JD et al., "Acquisition of real-time operation analytics for an automated serial sectioning system," *Integr. Mater. Manuf. Innov.* 2017;6:135-46.

Madison JD et al., "Advancing quantitative description of porosity in autogenous laser-welds of 304L stainless steel," *Integr. Mater. Manuf. Innov.* 2014;3:11 (17 pp.).

Madison JD et al., "Characterization of three-dimensional dendritic structures in nickel-base single crystals for investigation of defect formation," *Proceedings of the 11th International Symposium on Superalloys held on 14-18 Sep. 14-18, 2008 in Champion, Pennsylvania USA*, pp. 881-8.

Madison JD et al., "Coupling 3D quantitative interrogation of weld microstructure with 3D models of mechanical response," *Metall. Microstruct. Anal.* 2013;2(6):359-63.

Madison J et al., "Fluid flow and defect formation in the three-dimensional dendritic structure of nickel-based single crystals," *Metall. Mater. Trans. A* 2012;43(1):369-80.

Madison J et al., "Modeling fluid flow in three-dimensional single crystal dendritic structures," *Acta Materialia* 2010;58(8):2864-75.

Madison JD et al., "Porosity in millimeter-scale welds of stainless steel: three-dimensional characterization," *Sandia Report No. SAND2012-4474*, May 2012 (45 pp.).

Madison JD et al., "Quantitative characterization of porosity in laser welds of stainless steel," *Scripta Materialia* 2012;67(9):783-6.

Madison J et al., "The three-dimensional reconstruction of the dendritic structure at the solid-liquid interface of a Ni-based single crystal," *JOM* 2008;60(7):26-30.

Mangan MA et al., "Three dimensional investigation of Cu—Ti discontinuous precipitation," *Scripta Materialia* 1997;37(4):517-22.

Mangan MA et al., "Three-dimensional reconstruction of Widmanstätten plates in Fe-12.3Mn-0.8C," *J. Microsc.* 1997;188(1):36-41.

Maruyama B et al., "A new technique for obtaining three-dimensional structures in pitch-based carbon foams," *Scripta Materialia* 2006;54:1709-13.

Mendoza R et al., "The morphological evolution of dendritic microstructures during coarsening," *Metall. Mater. Trans. A* 2003;34A(3):481-9.

Spowart JE, "Automated serial sectioning for 3-D analysis of microstructures," *Scripta Materialia* 2006;55(1):5-10.

Spowart JE et al., "Collecting and analyzing microstructures in three dimensions: a fully automated approach," *JOM* 2003;55(10):35-7.

Spowart JE, "The 3-D analysis of discontinuously reinforced aluminum composite microstructures," *JOM* 2006;58(12):29-33.

Uchic M et al., "An automated multi-modal serial sectioning system for characterization of grain-scale microstructures in engineering materials," in: De Graef M, Poulsen HF, Lewis AC, Simmons JP, Spanos G (eds.), *1st International Conference on 3D Materials Science*, held on Jul. 8-12, 2012 in Seven Springs, PA, John Wiley & Sons, Inc. Hoboken, NJ, 2016, pp. 195-202.

Uchic MD et al., "Automated serial sectioning methods for rapid collection of 3-D microstructure data," *JOM* 2011;63(3):25-9.

Uchic MD, "Serial sectioning methods for generating 3D characterization data for grain- and precipitate-scale microstructures," in: Ghosh S and Dimiduk D (eds.), *Computational Methods for Microstructure-Property Relationships*, Springer Science+Business Media, LLC, New York, NY 2011, pp. 31-52.

UES, Inc., "Robo-Met.3D: A Fully Automated, Serial Sectioning System for Three-Dimensional Microstructural Investigations," 2015, Brochure No. R3D-003-022615, 2 pp.

UES, Inc., "Robo-Met.3D: Your Microstructures—Now in 3D," 2015, Brochure No. R3D-001-030315, 8 pp.

Wolfsdorf TL et al., "The morphology of high volume fraction solid-liquid mixtures: an application of microstructural tomography," *Acta Materialia* 1997;45(6):2279-95.

\* cited by examiner

HIGH RESOLUTION, NON-CONTACT REMOVAL RATE MODULE FOR SERIAL SECTIONING

CROSS-REFERENCE TO RELATED APPLICATION

This application claims the benefit of U.S. Provisional Application No. 62/393,950, filed Sep. 13, 2016, which is hereby incorporated by reference in its entirety.

STATEMENT OF GOVERNMENT INTEREST

This invention was made with Government support under contract no. DE-NA0003525 awarded by the U.S. Department of Energy to National Technology & Engineering Solutions of Sandia, LLC. The Government has certain rights in the invention.

FIELD OF THE INVENTION

The present invention relates to a metallographic system including a measurement module configured to provide precise differential measurements of a sample after serial sectioning, as well as methods of employing such a module. In particular examples, the measurement module provides a differential measurement without contacting the surface of a sample, thereby minimizing contamination of the sample surface.

BACKGROUND OF THE INVENTION

Mechanical serial sectioning is a highly repetitive technique employed in materials science (e.g., metallography) for rendering three-dimensional reconstructions of microstructure. While alternate techniques such as ultrasonic detection and micro-computed tomography have progressed much in recent years, few alternatives provide equivalent opportunities for comparatively high resolutions over significantly-sized cross-sectional areas and volumes. To that end, the introduction of automated serial sectioning systems has greatly heightened repeatability and increased data collection rates, while diminishing opportunity for mishandling and other user-introduced errors. Unfortunately, even among current, state-of-the-art automated serial sectioning systems, challenges in data collection have not been fully eradicated. Accordingly, there is a need for additional modalities that allow for real-time, accurate monitoring during such serial sectioning analysis.

SUMMARY OF THE INVENTION

The present invention, in part, provides real-time monitoring of material removal rates during a serial sectioning experiment. Also described herein are tools that identify interruptions or anomalies in data collection in conjunction with an automated, serial sectioning system. In one non-limiting embodiment, the systems herein employ a measurement module that provides precise differential measurement(s) of a sample after serial sectioning. Such measurement include, e.g., a differential between an unchanging reference height and a changing sample height. This differential relates directly to the amount of sample material removed by polishing the sample surface. As each newly polished surface is examined by the analyzer module (e.g., by use of an optical microscope), the image or data obtained for each polished surface can be correlated to the differential, which in turn provides a slice thickness. Additional details follow.

Definitions

As used herein, the term "about" means +/−10% of any recited value. As used herein, this term modifies any recited value, range of values, or endpoints of one or more ranges.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

DETAILED DESCRIPTION OF THE INVENTION

Figure 1:
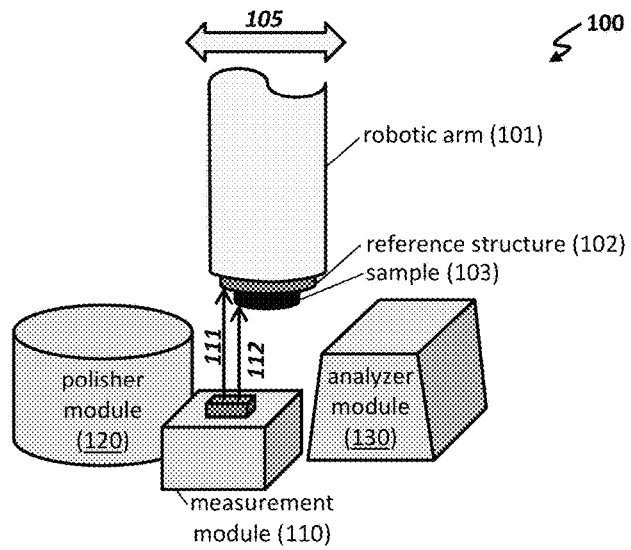
FIG. 1 shows an exemplary system 100 having a robotic arm 101, as well as a measurement module 110 configured to measure a reference distance 111 between the measurement module 110 and a surface of the reference structure 102. The measurement module 110 can also be configured to measure a sample distance 112 between the measurement module 110 and a surface of the sample 103. The system 100 can optionally include a polisher module 120 and an analyzer module 130.

The present invention relates, in part, to a measurement module configured to provide real-time differential measurements during a serial sectioning experiment of a sample. Such a module can provide more accurate distance measurements, which can improve data resolution, enhance data accuracy, and/or minimize errors. In one non-limiting embodiment, the measurement module is configured to measure a reference distance between the measurement module and a portion of the reference surface and to measure a sample distance between the measurement module and a portion of the surface of the sample. Such distances can be measured in any useful manner (e.g., by employing a laser-based interferometric or triangulation method). The reference distance can be configured, e.g., to be constant. In general, during a serial sectioning experiment, the sample is sectioned to provide a new surface, such that the sample distance is constantly changing throughout the experiment. Each new surface, or slice, can be examined to determine any useful physical and/or chemical characteristic (e.g., porosity, granularity, topography, tensility, conductivity, transparency, crystallinity, reflectivity, etc.). Then, data from each slice can be compiled to provide a three-dimensional reconstruction of the sample.

Each surface (e.g., planar surface) can be provided in any useful manner. In one instance, the surface is polished to provide a new surface. In another instance, the surface is milled, etched, and/or cut to provide a new surface. Prior to being examined, the surface (or new surface) can be cleaned, washed, rinsed, treated, and/or dried. Any surface, including new surface(s), of the sample can be examined in any useful manner (e.g., by determining any useful physical and/or chemical characteristic).

The present invention also relates to a system (e.g., a metallographic system, including an automated system thereof) having any useful number of modules. Exemplary modules includes a measurement module (e.g., configured to measure a reference distance and/or a sample distance), a polisher module (e.g., configured to prepare a surface or a new surface of the sample), an analyzer module (e.g., configured to provide one or more physical and/or chemical characteristics), a loader module (e.g., configured to contain one or more samples), a mounting module (e.g., configured to mount one or more samples), and/or a preparation module (e.g., configured to wash, rinse, clean, treat, and/or dry one or more samples). Movement of a sample between modules can be facilitated in any useful manner (e.g., by use of manual movement and/or automated movement by a robotic manipulator arm).

With respect to the measurement module, any useful reference distance or sample distance can be measured. In one non-limiting instance, the reference distance is a distance between the measurement module and a reference surface (or a portion thereof, e.g., a surface of a reference structure). In another non-limiting instance, the sample distance is a distance between the measurement module and a surface (or a portion thereof) of the sample.

The measurement module can include any useful component(s) to maintain the reference distance and/or to measure any useful distance. Exemplary components include a mount (e.g., a three-axis mount) configured to maintain a sensor capable of providing distance measurements in a non-contact manner. An exemplary sensor includes a laser interferometer (see, e.g., FIG. 4B).

The polisher module can be used to prepare a sample surface in any useful manner, including, e.g., rough polishing, fine polishing, laser treatment, plasma treatment, application of a lubricant, and/or cleaning of the surface. In one non-limiting instance, the polisher module provides sections of a sample by removing a thin layer of material from the sample, while keeping the new sample surface flat, parallel, and free from scratches and other surface defects such that it can be imaged (e.g., by using an optical microscope in reflective mode). The module can have any useful components, such as a platen (e.g., a flat platen covered by a polishing film optionally including diamond and/or an abrasive powder), a polishing cloth or pad, and/or a lubricant. Rotation of a platen against a surface of the sample can remove material, thereby providing a new surface for further examination. The sample can be maintained within the polisher module by affixing the sample (e.g., affixing the sample onto a handling mount, such as one including a substrate, molded epoxy, adhesive, support, and/or mounting clip) or by holding the sample against a platen (e.g., by use of a robotic arm).

Exemplary components for an analyzer module include an optical microscope (e.g., use of dark-field optical microscopy, bright-field optical microscopy, polarized-light optical microscopy, differential interference contrast microscopy, and/or confocal laser microscopy), an electron microscope (e.g., use of scanning electron microscopy), an optical camera, a charge coupled device (CCD) camera, an X-ray camera, a spectroscope (e.g., use of Raman spectroscopy, infrared spectroscopy, NMR spectroscopy, X-ray spectroscopy, and/or photoelectron spectroscopy), as well as real-time and/or automated forms thereof.

A loader module can be configured to contain one or more samples in any useful manner. In one non-limiting instance, the loader module can include a carousel to hold or receive a plurality of samples. A mounting module can be configured to mount one or more samples. In one non-limiting instance, the mounting module can include an adhesive supply, a nozzle configured to dispense an adhesive from the adhesive supply, and a mounting clip configured to be affixed to a surface of the sample by use of the adhesive (e.g., a bottom surface of the sample, where the top surface of the sample is employed for further examination by the analyzer module).

The preparation module can be used to wash, rinse, clean, treat, and/or dry one or more samples, including, e.g., cleaning (such as ultrasonic cleaning, chemical etching, electrolytic etching, etc.), rinsing, and/or drying (such as with compressed nitrogen gas) the sample, as well as automated forms thereof. The system can further include a sectioning saw, e.g., incorporated within any module described herein or provided in a separate module configured to be accessed by the robotic arm.

FIG. 1 shows a non-limiting, exemplary system 100 having a measurement module 110, a polisher module 120, and an analyzer module 130. A robotic arm 101 is employed to move 105 (e.g., horizontally and/or vertically translate) a sample 103 between each module. The arm 101 is also configured to maintain the sample 103 at its distal portion. The arm 101 also includes a reference structure 102 in proximity to the sample 103 and at its distal portion. The reference structure can have any useful architecture, such as a machined ring affixed in a stationary manner to a distal portion of the arm 101.

In this exemplary system 100, the arm 101 is configured to maintain a reference distance 111 that is fixed. This exemplary reference distance 111, in turn, is the vertical distance between a portion of the reference structure 102 and a sensor of the measurement module 110 configured to measure this vertical distance. The arm 101 also maintains a sample 103 at its distal portion, and the sample distance 112 can also be measured. This exemplary sample distance 112 is the vertical distance between a surface (or a portion thereof) of the sample 103 and a sensor of the measurement module 110 configured to measure this distance. As described herein, a serial sectioning experiment proceeds by removing material from a surface of the sample and then examining the surface of any useful characteristic. At each surface (and new surface formed by material removal), an analysis is conducted for each section, and then each section-based analysis is compiled to provide a three-dimensional (3D) reconstruction of the sample. The accuracy of the reconstruction can depend on an accurate measurement of the thickness of the section or slice. This thickness can be determined in real-time by, e.g., the differential between the fixed reference distance and the ever-increasing sample distance as the sample is sectioned (e.g., by polishing).

In one non-liming instance, the measurement module 110 is configured to measure a reference distance 111 between the measurement module and a surface of the reference structure 102 and configured to measure a sample distance 112 between the measurement module and a surface of the sample 103.

Figure 2:
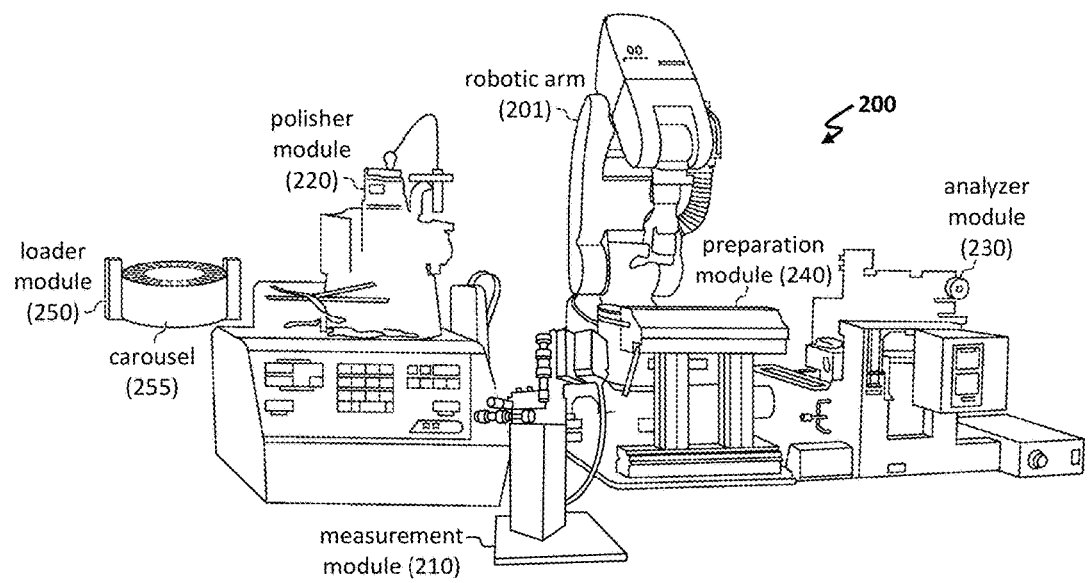
FIG. 2 shows another exemplary system 200 having a robotic arm 201, a measurement module 210, a polisher module 220, an analyzer module 230, an optional preparation module 240, and an optional loader module 250.

The system can have any number of other useful modules. As seen in FIG. 2, a non-limiting, exemplary system 200 can include a robotic arm 201 configured to move a sample from and to any of the following modules in any useful order: a loader module 250 having a carousel 255 configured to store one or more samples, a polisher module 220 configured to polish a surface of a sample, a measurement module 210 configured to provide a reference distance and/or a sample distance after polishing, a preparation module 240 configured to prepare the sample, and/or an analyzer module 230 configured to examine the sample. Other exemplary systems and modules are described herein (see, e.g., in FIG. 4A-4B and FIG. 5A-5C).

The system can include a processing unit to control or operate one or more modules. The processing unit may have a computer-readable medium and a processor. The computer-readable medium (e.g., memory) may have a stored algorithm that is used by the processor to algorithmically evaluate data (e.g., sectional data obtained by use of the analyzer module). The computer-readable medium may include any useful software, e.g., serial sectioning process control software to provide control over any one or more modules or robotic arm; or 3D microstructure volume rendering software to provide digital analysis of the sample using any data obtained by the system (e.g., sectional data obtained for each section). A computer-usable or computer-readable medium may be any medium that can contain, store, communicate, propagate, or transport the program for use by or in connection with the instruction execution system, apparatus, or device. The processing unit can also include any useful interface to provide any useful data obtained by or from the system (e.g., a graphical user interface, as shown in FIGS. 8-11).

The processing unit can be configured to perform any useful function, e.g., digital imaging of the sample, reconstructing the sample using data from the analyzer module, mapping one or more crystallographic orientations determined from the sample surface, running 3D microstructure volume rendering software to provide real-time 3D microstructure software data of the sample, conducting image analysis and/or pattern recognition algorithms on collected data or reconstructed data, and/or conducting cross-correlation techniques (e.g., Fast Fourier Transform (FFT)-based techniques) to analyze and align data sets, as well as any step of any method described herein. Algorithms disclosed herein (e.g., including any algorithm configured to perform any method described herein) may be embodied in hardware and/or in software (including firmware, resident software, micro-code, etc.).

The system can also include a programmable controller (e.g., configured to control the robotic arm, the measurement module, the analyzer module, the polisher module, the loader module, and/or the preparation module; configured to perform image analysis and to position the sample for examination by the analyzer module based on feedback from the measurement module; configured to control the robotic arm to manipulate the sample between two or more modules, e.g., between the measurement module and the analyzer module; configured to provide a predetermined degree of polishing by the polisher module; and/or configured to measure the reference distance and the sample distance by the measurement module). The controller may have at least one processor and a computer-readable medium.

The system and modules described herein (see, e.g., FIG. 4A), as well as any tools herein, can be used in conjunction with any useful metallographic system and methods thereof, such as any described in U.S. Pat. Nos. 7,317,964, 7,319,914, 7,319,915, and 7,319,916, as well as U.S. Pat. Pub. No. 2014/0130613, each of which is incorporated herein by reference in its entirety, including, but not limited to, their description of the components of the automated metallographic system such as sample preparation, serial sectioning, polishing, cleaning, etching, imaging, image acquisition, and microstructural analysis of materials, as well as related hardware control software routines.

Methods

The present invention also relates to methods for examining a surface of the sample. The method can include a step of obtaining a reference distance and a sample distance, thereby determining a section or slice thickness by calculating a differential between the reference distance and the sample distance. In particular non-limiting embodiments, the method further includes steps to obtain new sample surfaces, which provides new sample distances and new section or slice thicknesses.

In one non-limiting instance, the method includes manipulating a sample to a measurement module, where the measurement module is configured to measure a reference distance (e.g., a first reference distance) between the measurement module and a portion of a reference surface and to measure a sample distance (e.g., a first sample distance) between the measurement module and a portion of a surface of the sample (e.g., a first surface); obtaining the reference distance and the sample distance; manipulating the sample to an analyzer module configured to examine the surface of the sample; and examining the first surface of the sample. The method can include further steps to provide further surfaces (e.g., a second surface of a sample, a third surface of a sample, etc. obtained by sectioning and/or polishing) and further distances (e.g., a second sample distance, a third sample distance, etc.), as well steps to examine such surfaces and measure such distances. Additional steps include manipulating a sample (e.g., by use of a robotic arm) to any useful module, such as a module configured to perform a measuring step (e.g., by a measurement module) or an examining step (e.g., by an analysis module).

Figure 3A:
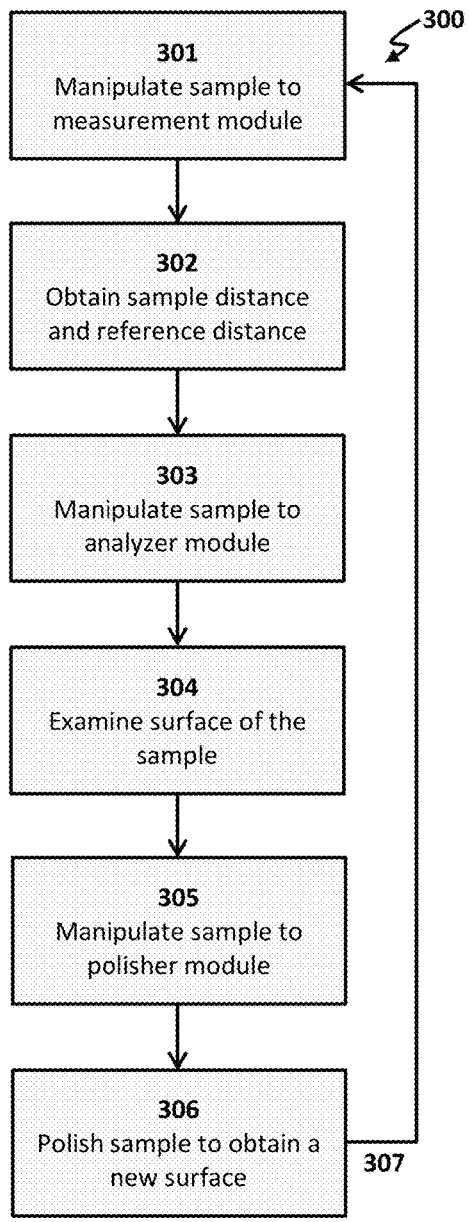
FIG. 3A-3B shows an exemplary first method 300 (FIG. 3A) and an exemplary second method 310, which can include the steps of manipulating a sample to a measurement module 301,313 and obtaining a sample distance and a reference distance 302,314.

FIG. 3A provides a non-limiting, exemplary method 300 that includes manipulating 301 a sample to a measurement module (e.g., configured to obtain any useful reference distance and/or sample distance), obtaining 302 a sample distance and a reference distance, manipulating 303 the sample to an analyzer module (e.g., configured to examine a surface of the sample), examining 304 a surface (e.g., a first surface) of the sample, manipulating 305 the sample to a polisher module (e.g., configured to provide a second surface of the sample), polishing 306 the sample to obtain a new surface (e.g., a further surface, such as a second, third, fourth, etc., surface), and then repeating 307 any useful step (e.g., thereby obtaining a further sample distance and/or a further reference distance for each further surface obtained by polishing the sample, and thereby providing examination of each slice or section obtained by polishing the sample).

The steps can be performed for any useful number of iterations to provide an n number of polished surfaces for any n number of sections obtained from the sample. Exemplary n include any integer of from about 1 to 1,000. In addition, each step can be performed in any useful order. FIG. 3A provides a method in which the first surface is examined without requiring polishing. In contrast, FIG. 3B provides another method 310 in which the first surface is obtained by polishing 312 and then is later examined 316.

Figure 3B:
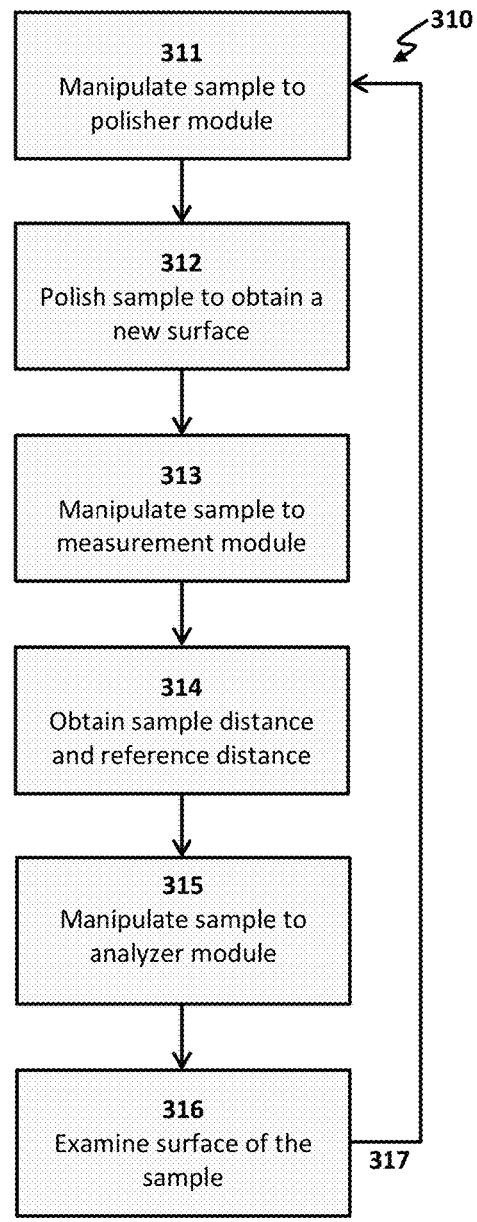

FIG. 3B provides a non-limiting, exemplary method 310 that includes manipulating 311 a sample to a polisher module (e.g., configured to provide a first surface of the sample), polishing 312 the sample to obtain a new surface (e.g., a first surface), manipulating 313 a sample to a measurement module (e.g., configured to obtain any useful reference distance and/or sample distance), obtaining 314 a sample distance and a reference distance, manipulating 315 the sample to an analyzer module (e.g., configured to examine a surface of the sample), examining 316 a surface (e.g., a first surface) of the sample, and then repeating 317 any useful step (e.g., thereby obtaining a further sample distance and/or a further reference distance for each further surface obtained by polishing the sample, and thereby providing examination of each slice or section obtained by polishing the sample). Sample distances and/or reference distances can be obtained before and/or after the analyzing step.

Any method herein can be performed by a user (e.g., operating any system described herein) or an algorithm configured to perform each step of the method (e.g., by way of executable code for use with a processing unit).

EXAMPLES

Example 1: High Resolution, Non-Contact Removal Rate Monitor for Serial Sectioning We have developed a high resolution, non-contact method for determining material removal rates with high accuracy (e.g., within order of +/−one micron). Such a method or apparatus encompassing such a method could be used in conjunction with any useful system, such as an automated serial sectioning system (e.g., a Robo-Met.3D® system, including the non-limiting system depicted in FIG. 4A). The method and/or apparatus can combine a laser, a custom-made three-axis stage, and a machined reference structure (e.g., a machined ring) to measure differential between a sample-specific distance (e.g., a sample height) and a reference-specific distance (e.g., a reference height), such as the non-limiting depicting in FIG. 4B.

Typically, the sample-specific distance is measured between a position of the emitted laser and a portion of a surface of the sample, and the reference-specific distance is measured between a position of the emitted laser and a portion of a surface of the reference structure. Throughout the serial sectioning experiment, the sample surface is sectioned (e.g., by polishing or cutting the sample), thereby providing a renewed surface for examination. In this manner, each surface (or slice) can be examined in any useful manner (e.g., by way of an optical microscope or any other useful technique), and then each slice can be compiled to provide a three-dimensional reconstruction of the tested sample.

Figure 5A:
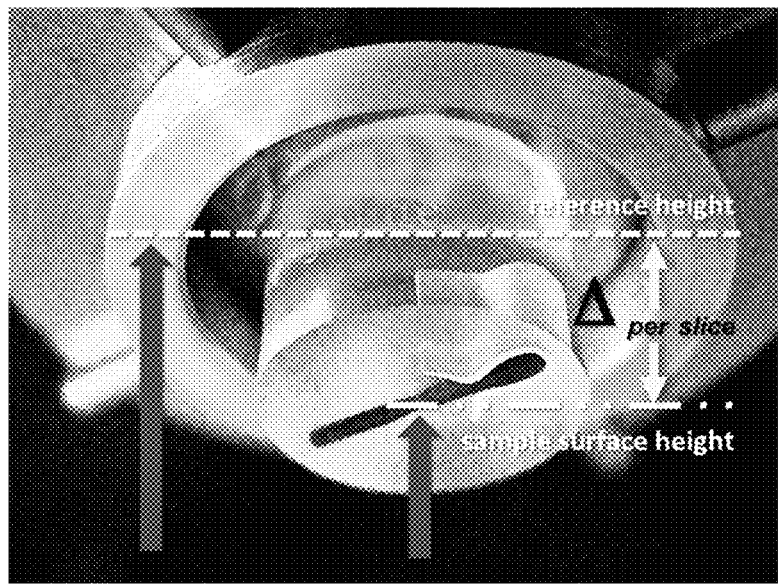
FIG. 5A-5C shows various exemplary depictions of the reference structure and the sample, each of which is disposed on a distal end of a robotic arm. Provided are a photograph of a measurement differential (here, e.g., Δ per slice) between an exemplary reference distance (here, e.g., a reference height) and an exemplary sample distance (here, e.g., a sample surface height) (FIG. 5A); a photograph of the distal end of a robotic arm in proximity to a laser interferometer system of the measurement module (FIG. 5B); and a photograph of the laser measurement module, sample, and sample mount within the Robo-Met.3D® enclosure (FIG. 5C).
Figure 5B:
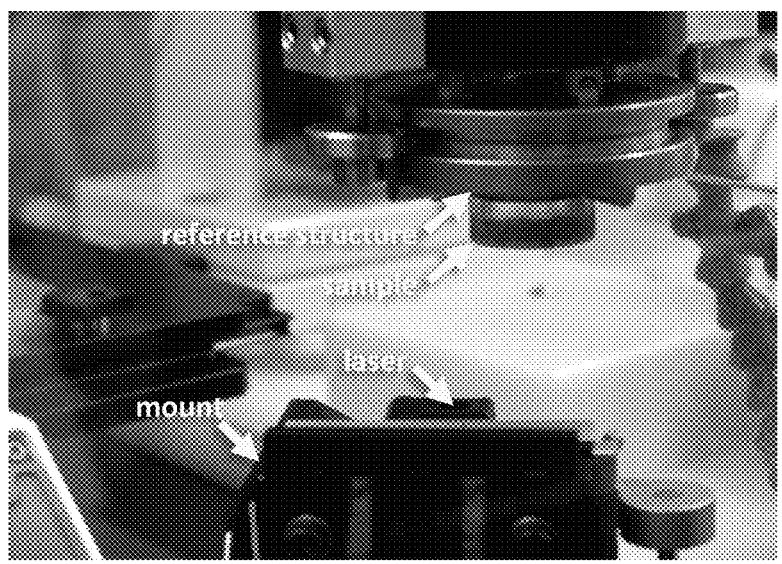
Figure 5C:
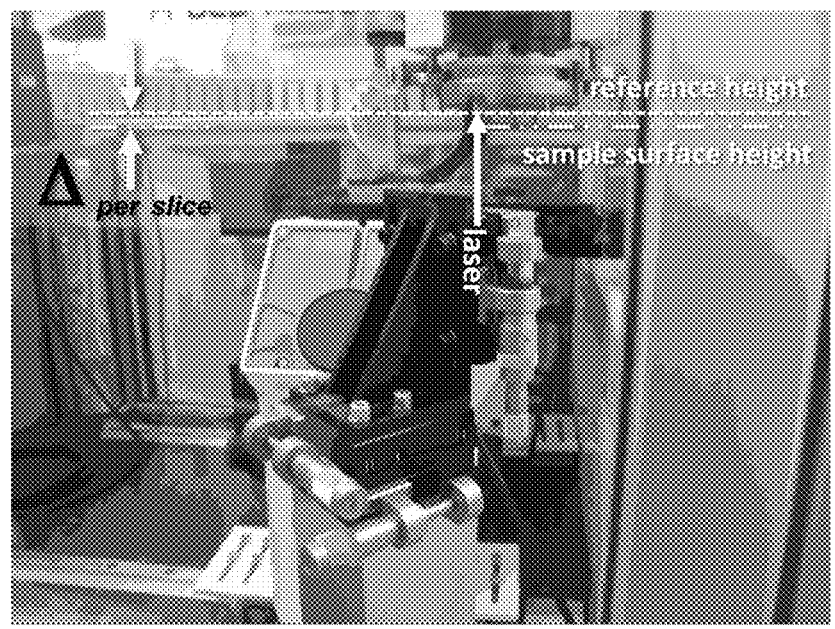

In particular embodiments, a laser interferometer system with a sensor head can be incorporated into an enclosure for a metallographic system (e.g., a Robo-Met.3D® system) via a customized three-axis, micron-resolution stand to provide a secondary measure of removal rate (see, e.g., FIG. 5C). The measurement can be based on the differential between an unchanging reference height achieved by affixing a machined reference structure directly to the sample translation puck and the height of the sample surface throughout the serial sectioning experiment (see, e.g., FIG. 5A-5B). In specific embodiments, the apparatus and/or method (e.g., a measurement module and/or a method employing such a module) can require no physical contact with the sample and is very repeatable within microns. The sensor head can be chosen to have any useful measurement range (e.g., of from about 1 mm to about 50 mm) and useful resolution (e.g., about +/−1 micron). Additional details are provided herein.

Example 2: Acquisition of Real-Time Operation Analytics for an Automated Serial Sectioning System The earliest example of serial sectioning in materials science dates back to the early 1900's with the work of Otto Forsman's investigation of ferrous pearlite (see, e.g., Forsman O, "Undersokning av rymdstrukturen hos ett kolstal av hypereutektoid sammansattning," *Jernkontorets Annaler* 1918; 102:1-30). Decades later in 1962, Hillert used serial sectioning to evaluate the shape of pearlitic ferrite in steel (see, e.g., Hillert M, "The formation of pearlite" in: Zackay V F, Aaronson H (eds.), *Decomposition of austenite by diffusional processes,* 1962, Wiley Interscience, New York, N.Y., pp. 197-247), while Caron applied the technique to better understand the shapes and sizes of grains in a titanium alloy in a thesis dissertation in 1970 (see, e.g., Caron R N, "Tempering and recovery of iron-0.2C martensite," *Academic dissertation*, Lehigh University, Bethlehem, Pa., 1970).

However in 1991, the application and occurrences of mechanical serial sectioning within the materials science literature increased dramatically beginning with the work of Hull and co-workers (see, e.g., Hull D A et al., "Titanium prior-beta grain volume distribution by quantitative serial sectioning techniques," *Mater. Character.* 1991; 26(2):63-71) and continuing on with the efforts of Mangan and Shiflet (see, e.g., Mangan M A et al., "Three-dimensional reconstruction of Widmanstätten plates in Fe-12.3Mn-0.8C," *J. Microsc.* 1997; 188(1):36-41; and Mangan M A et al., "Three dimensional investigation of Cu—Ti discontinuous precipitation," *Scripta Materialia* 1997; 37(4):517-22), Kral and Spanos (see, e.g., Kral M V et al., "Three-dimensional analysis of microstructures," *Mater. Character.* 2000; 45(1):17-23; Kral M V et al., "Three-dimensional analysis of proeutectoid cementite precipitates," *Acta Materialia* 1999; 47(2):711-24; Kral M V et al., "Three-dimensional analysis and classification of grain-boundary-nucleated proeutectoid ferrite precipitates," *Metall. Mater. Trans. A* 2005; 36A(5):1199-207; and Kral M V et al., "Three-dimensional morphology of cementite precipitates," *Scripta Materialia* 1997; 36(8):875-82), and Voorhees and co-workers (see, e.g., Wolfsdorf T L et al., "The morphology of high volume fraction solid-liquid mixtures: an application of microstructural tomography," *Acta Materialia* 1997; 45(6):2279-95; Alkemper J et al., "Three-dimensional characterization of dendritic microstructures," *Acta Materialia* 2001; 49(5):897-902; Alkemper J et al., "Quantitative serial sectioning analysis," *J. Microsc.* 2001; 201(3):388-94; Lund A C et al., "The effects of elastic stress on microstructural development: the three-dimensional microstructure of a γ-γ' alloy," *Acta Materialia* 2002; 50(10):2585-98; and Mendoza R et al., "The morphological evolution of dendritic microstructures during coarsening," *Metall. Mater. Trans. A* 2003; 34A(3):481-9). One chief significance of each of the aforementioned efforts has been each work's contribution to the field in advancing the methods of data collection or the processes used for reconstruction of mechanical serial sectioning data.

One such advance was the introduction of the first fully automated serial sectioning system by Alkemper and Voorhees (see, e.g., Alkemper J et al., "Quantitative serial sectioning analysis," *J. Microsc.* 2001; 201(3):388-9). The system combined a diamond blade micro-miller, a micron-sensitive three-axis stage, and a linear variable differential transformer for alignment, registration and depth measurement. While the first of its kind, its applications were largely focused on relatively "soft" metallic systems, such as Al—Cu and Pb—Sn. Spowart and Mullens later developed an automated approach to serial sectioning combining a 6-axis robotic arm, an inverted microscope, an ultrasonic bath, and a polishing wheel with interchangeable diamond abrasive films (see, e.g., Spowart J E et al., "Collecting and analyzing microstructures in three dimensions: a fully automated approach," *JOM* 2003; 55(10):35-7; Spowart J E, "Automated serial sectioning for 3-D analysis of microstructures," *Scripta Materialia* 2006; 55(1):5-10; and Spowart J E, "The 3-D analysis of discontinuously reinforced aluminum composite microstructures," *JOM* 2006; 58(12):29-33). UES, Inc. later purchased the rights to license this tool, commercialized the unit, and have deployed units worldwide (see, e.g., Uchic M et al., "An automated multi-modal serial sectioning system for characterization of grain-scale microstructures in engineering materials," in: De Graef M, Poulsen H F, Lewis A C, Simmons J P, Spanos G (eds.), *1st International Conference on 3D Materials Science*, held on 8-12 Jul. 2012 in Seven Springs, Pa., John Wiley & Sons, Inc., Hoboken, N.J., pp. 195-202).

In 2012, an alternative automated serial sectioning system (Genus_3D™) was reported by Adachi et al. (see, e.g., Adachi Y et al., "Development of fully automated serial-sectioning 3D microscope and topological approach to pearlite and dual-phase microstructure in steels," in: De Graef M, Poulsen H F, Lewis A C, Simmons J P, Spanos G (eds.), *1st International Conference on 3D Materials Science*, held on 8-12 Jul. 2012 in Seven Springs, Pa., John Wiley & Sons, Inc., Hoboken, N.J., pp. 37-42), however very little is available in the literature, at this time, regarding this system.

The following tools presented herein are generally adaptable to any mechanical serial sectioning data set, provided a specific ordering of data is available. The tools were validated using a Robo-Met.3D® system for three-dimensional microstructural investigations, therefore, the tools presented herein will be presented with the Robo-Met.3D® as context. However, the tools herein can be employed with any useful data set or any useful serial sectioning system.

Figure 4A:
FIG. 4A-4B shows photographs of a Robo-Met.3D® system (FIG. 4A) and an exemplary measurement module (FIG. 4B) having a three-axis stage mount for a laser interferometer.

In its basic configuration, the Robo-Met.3D® (version 2) combines and integrates a motorized metallographic polisher, a dual ultrasonic bath, a ZEISS™ inverted microscope, and a multi-axis robotic arm for translation of a single mounted sample through each of the aforementioned stations for metallographic preparation (see, e.g., ROBO-MET.3D®, UES Inc., Dayton, Ohio, ues.com/content/robomet3d, last accessed Aug. 23, 2016). The entire system in located within a windowed enclosure to allow safe autonomous operation following the input of a user defined preparation routine. The user also specifies the number of cycles for the routine that is to be executed. An exemplary Robo-Met.3D® system is shown in FIG. 4A.

While autonomous and continuous operation for hours is typical, little is offered in terms of user feedback should an anomaly occur with respect to the sample or should an interruption occur with respect to the system. Either instance can presumably lead to damaged samples, lengthened data collection times, and, in some cases, unnecessary use of metallographic preparation consumables. Additionally, the system's primary method for measuring removal rate is based on the average focus height for each slice, which can be problematic if image quality is inconsistent or if the cross-sectional area of the region of interest is not uniform throughout the experiment. As such, the tools presented herein provide alternative means to mitigate these difficulties within automated serial sectioning systems, as well as provide to the user a richer context for real-time data collection.

Non-Contact Measurements of Material Removal

By design, the Robo-Met.3D® system uses a per slice average auto-focus height to approximate material removal rates throughout a serial sectioning experiment. This method is generally acceptable, provided that the sample being interrogated maintains a uniform cross-sectional area throughout the process and that image quality in each slice is relatively similar. For cases in which the full silhouette boundary contained within the serially sectioned image changes in size, this subtlety can make a profound difference in the estimated removal rate, thereby adversely biasing the measurement, resulting in an inaccurate value. For example, when the surface area becomes larger in subsequent slices, the estimated removal rate proposed by the average auto-focus can in fact provide a negative removal rate. To address this problem and provide a secondary measure with added fidelity, a laser has been integrated into the system. In particular, the laser system operates along the robotic arm's arc of travel in order to provide a measurement that is insensitive to changes in the cross-sectional area of samples.

Figure 4B:
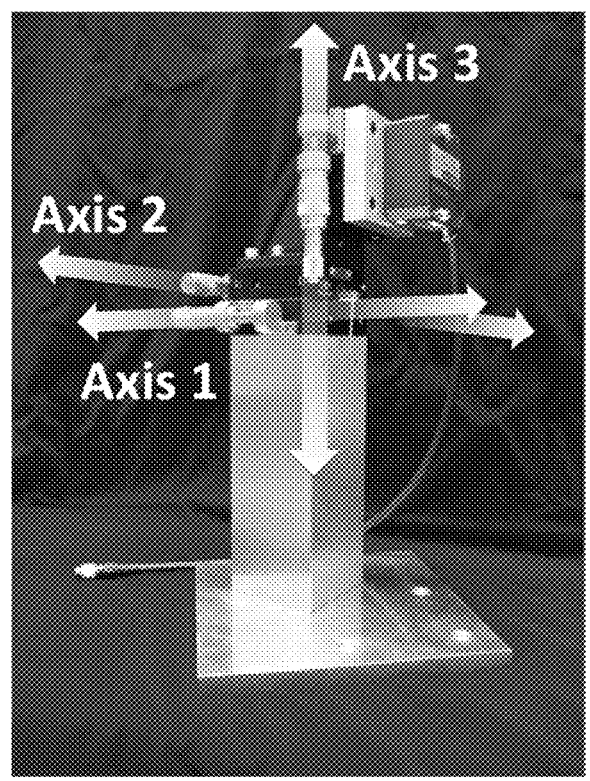

A KEYENCE™ laser interferometer system using a LK-H057 sensor head was incorporated into the Robo-Met.3D® enclosure via a custom three-axis, micron-resolution stand, as shown in FIG. 4B. The measurement is based on the difference between an unchanging reference height relative to the sample holder and the height of the sample surface, which constantly recedes throughout the serial sectioning experiment (FIG. 5A). The method requires no physical contact with the specimen and is repeatable to within a few microns. The sensor head itself has a measurement range of 50±10 mm and is interchangeable with other KEYENCE™ sensor heads having varied ranges and resolutions (see, e.g., available from Keyence Corp., Itasca, Ill., keyence.com/usa.jsp, last accessed Aug. 23, 2016). Schematics of the three-axis mount and a laser positioned below a sample within the Robo-Met.3D® are shown in FIG. 5B-5C. The exemplary reference structure is a machined ring disposed in proximity to the sample, in which the sample is disposed within the center of the ring (FIG. 5B). A laser beam is emitted from the sensor head, which is then reflected off of a surface (e.g., a surface of the reference structure or the sample) and then transmitted to a light-receiving element of the sensor, thereby providing a distance measurement (FIG. 5C).

Figure 6A:
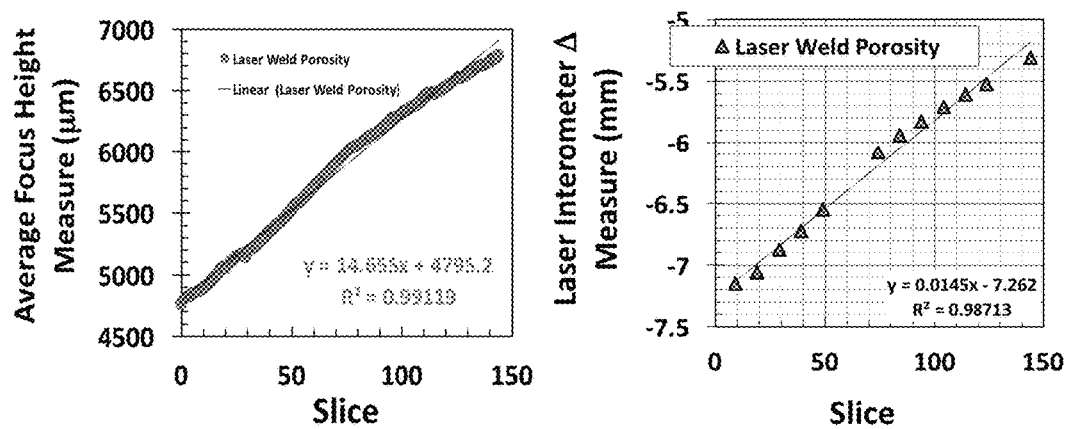
FIG. 6A-6C shows serial sectioning material removal rates measured by average focus height (left) and confirmed by non-contact laser interferometer measurements (right) for porosity in laser welds of a 304L stainless steel sample (FIG. 6A), geological formations of a sandstone sample (FIG. 6B), and a thermal spray coating of 304L stainless steel on stainless steel substrate (FIG. 6C).
Figure 6B:
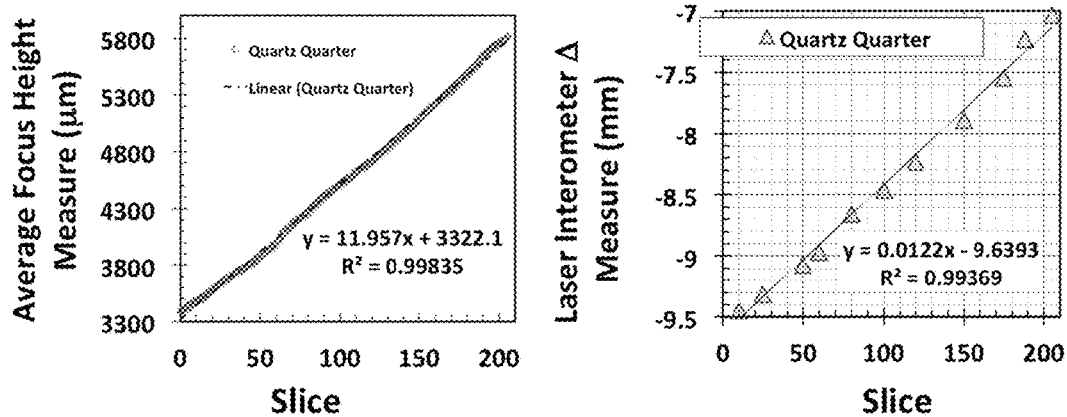
Figure 6C:
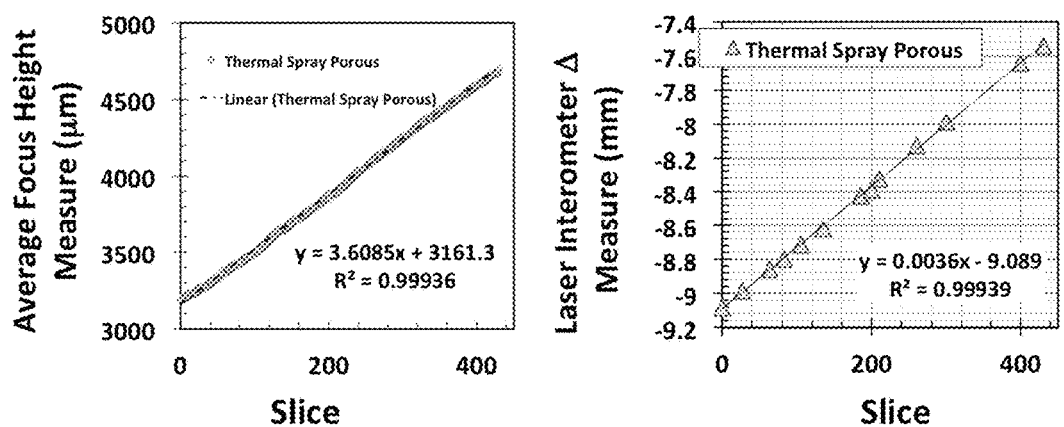
Figure 7A:
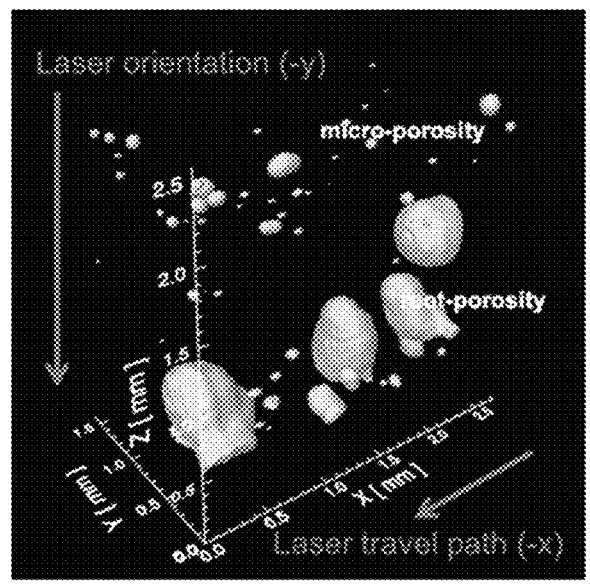
FIG. 7A-7C shows 2D optical micrographs and accompanying 3D reconstruction of laser weld porosity in a 304L stainless steel sample (FIG. 7A), sandstone grains in a geological formation (FIG. 7B), and a thermal spray coating of 304L stainless steel on a stainless steel substrate (FIG. 7C).
Figure 7B:
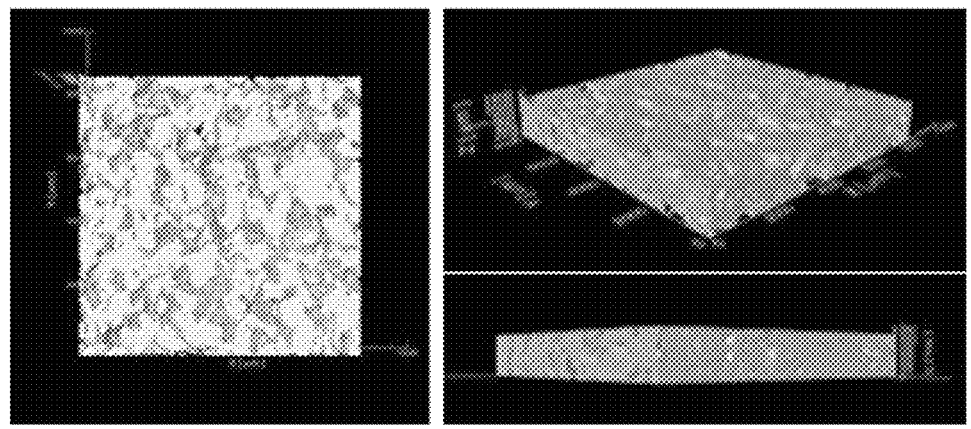
Figure 7C:
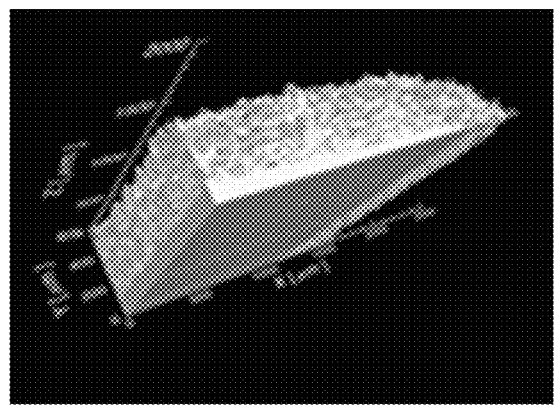

To demonstrate the validity of the technique, a series of control experiments were performed, in which the cross-sectional area of the sample was maintained throughout serial sectioning. Multiple series of intermittent, independent laser measurements compared well against the system's conventional measure across a variety of material systems, including examination of porosity in a laser weld (FIG. 6A), examination of geological formations in sandstone (FIG. 6B), and examination of a thermal spray coating on a substrate (FIG. 6C). As a reference, the three-dimensional reconstructions from the data acquisitions denoted in FIG. 6A-6C are shown here in FIG. 7A-7C, respectively.

Data Collection Monitor

Autonomous operation of any metallographic serial sectioning system is paramount to its benefit. As such, the performance of automated serial sectioning systems is chiefly accompanied by an expectation of lengthy and unsupervised operation. To increase efficiency during user absence, we have developed a set of software tools have been developed to provide real-time tracking of data acquisition, operational cycle times, as well as electronic user notifications in the event of an unintended system error or pause.

Using LabVIEW™, an extensible, graphical user interface with multiple panes was created for visualization of the aforementioned items through appropriation of the Robo-Met.3D® generated text data files. In this regard, the input data source is flexible. The tools described below simply require parsable text data that describe the serial sectioning experiment with the expectation of a certain ordering of data attributes per slice. Thus, the data input can quite presumably be produced from a variety of sources.

Figure 8:
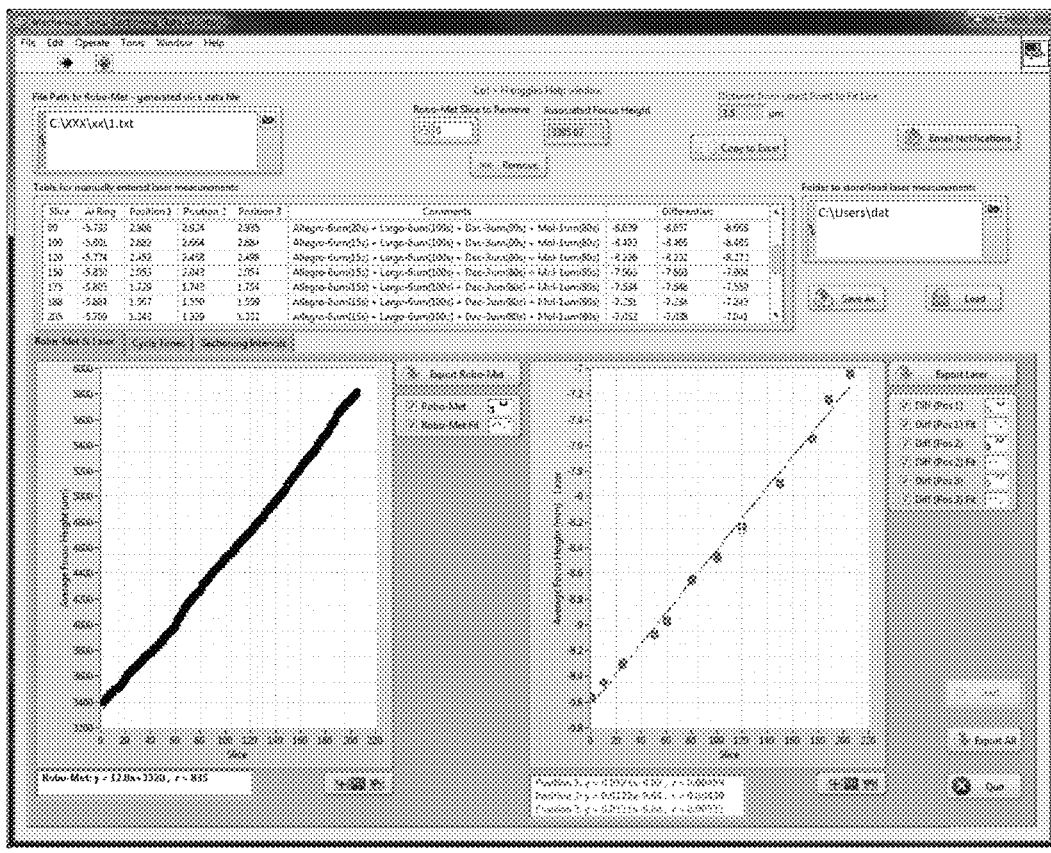
FIG. 8 shows a pane of an exemplary graphical user interface showing two independent removal rate measurements.
Figure 9:
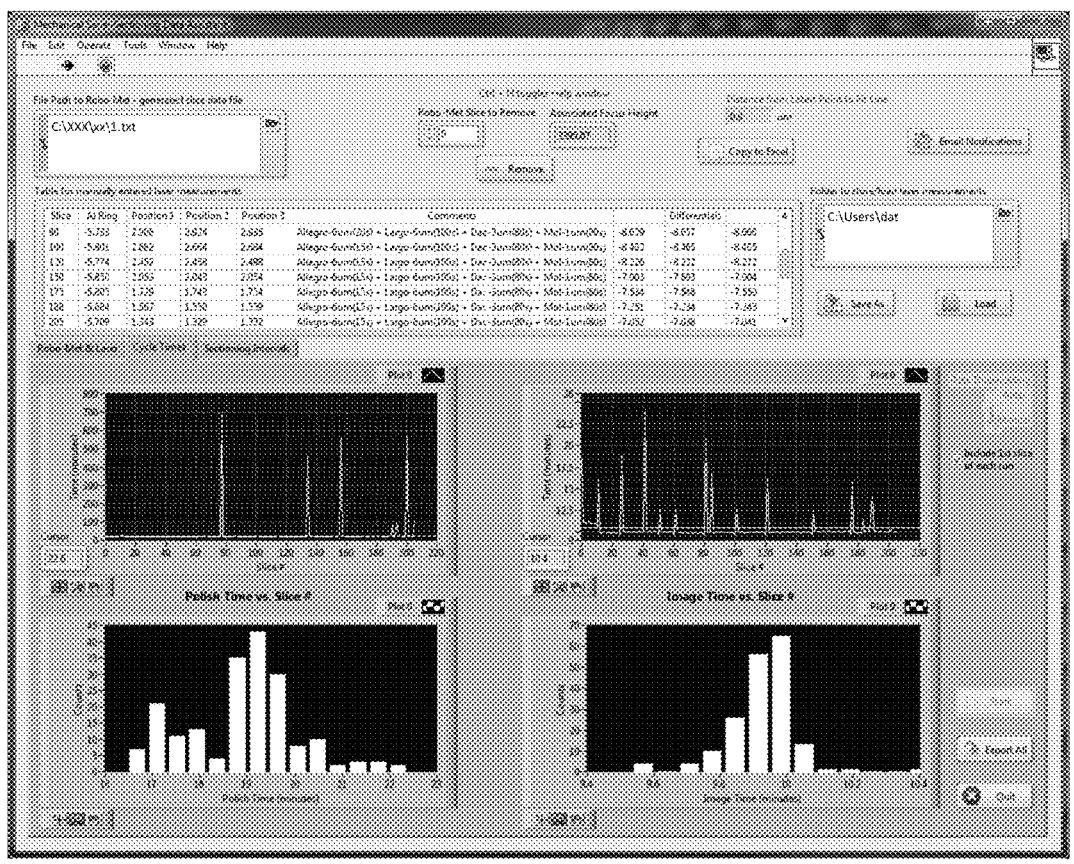
FIG. 9 shows another pane of an exemplary graphical user interface showing cycle times as a function of slice number for polishing and imaging.

The main tab of the graphical user interface, which is called the Mechanical Serial Sectioning Data Assistant (or MECH-SSDA), provides a real-time visual of the material removal rates acquired by both the average montage focus height as well as the laser interferometer, as often as new data is collected for either (FIG. 8).

Furthermore, since most automated serial sectioning systems can be generally divided into two primary steps, polishing and imaging, the second tab of MECH-SSDA (FIG. 9) provides a quantitative monitoring of cycle times associated with each polishing and each imaging interval, respectively. While polishing and imaging data are recorded for every slice, the collective aggregate of cycles times are provided by histogram to allow a user to quickly determine the frequency of cycle times specifically associated with either polishing or imaging.

Figure 10:
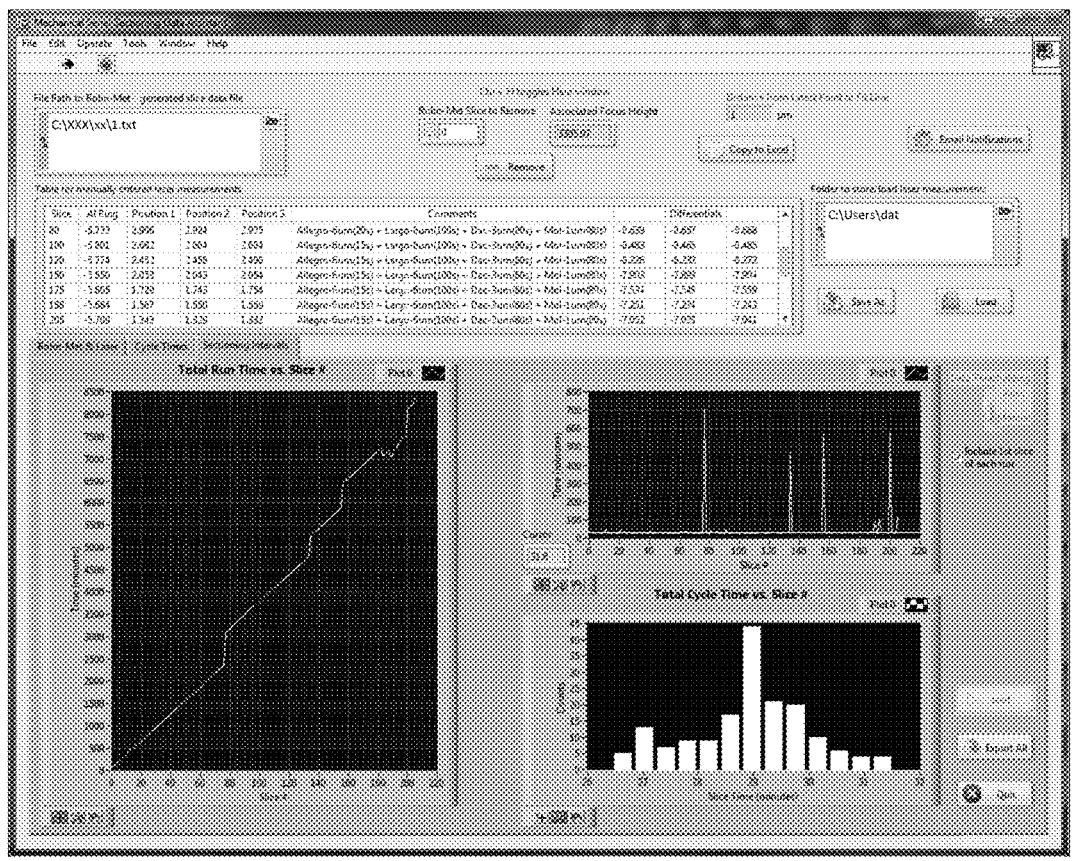
FIG. 10 shows yet another pane of an exemplary graphical user interface showing aggregate data collection time and total cycle times for each serial section (or slice) that was collected.

The third tab provides an aggregate view of the temporal footprint of the entire serial sectioning experiment as a function of serial sections (or "slices") acquired (FIG. 10). Here, in addition to the total experiment time expended, the user is afforded an immediate and visually identifiable measure of the time expended for the collection of each slice within the overall experiment.

Most plots within panes 2 and 3 of MECH-SSDA illustrate a measured quantity as a function of slice number, so that slice-by-slice behavior can be surmised. As can be observed, the peaks within the polishing time plots (FIG. 9) and the discontinuities within the total run time plot (FIG. 10) correspond directly for given outliers according to their slice number. These instances denote lengthy pauses in system operation due to the completion of a set during an over-night run prior to continued operation of the system during the next work day.

Additionally, within the lower sections of panes 2 and 3, all data are also plotted as real-time histograms, which can be adjusted by clicking and dragging up or down on the line appearing within the plot to eliminate outlier data points or to zoom in on specific portions of the data. Such real-time adjustments can assist in identifying the most frequently recurring time intervals or range of intervals for a given action.

Figure 11:
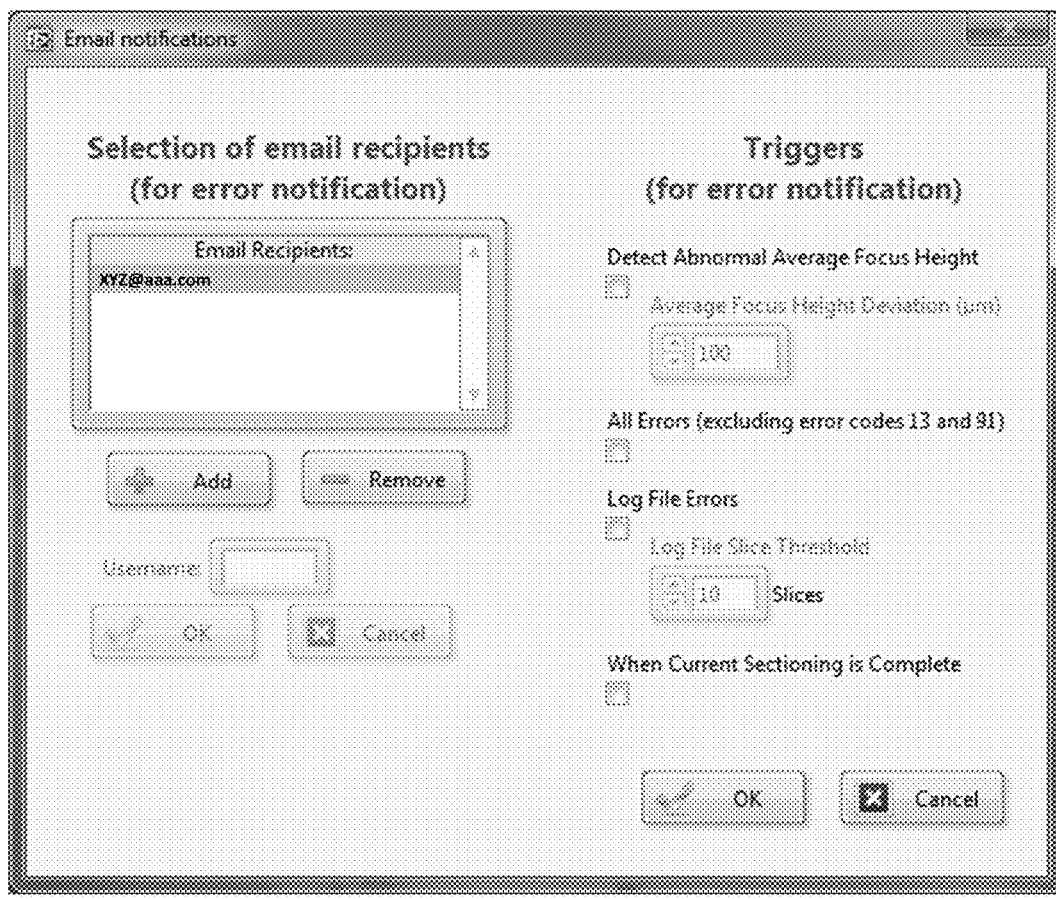
FIG. 11 shows another pane of an exemplary graphical user interface showing email notification options to any user for any useful trigger or error notification.

Lastly, using a variety of criteria readily quantifiable from the acquired data, MECH-SSDA can also send any number of users an email in the event certain events present themselves (FIG. 11). A listing of the selectable events currently available in version 1.3 of MECH-SSDA are shown in Table 1.

TABLE 1

Current Electronic User Messaging Options

| Event | Customizable Criteria | Argument or Units |
| --- | --- | --- |
| Abnormal Material Removal Rate | Deviation (+/−) from average | Microns |
| System Errors | Exclude errors of insignificance | Error Code Numbers |
| Log File Error | Disregard known log abnormalities external to system operation | Log Index Values |
| Completion of Experiment | — | — |

Discussion

Automated serial sectioning systems present a definite advance in metallographic preparation toward three-dimensional interrogations of microstructure. However, due to the lengthy and often costly investment required for data collection, tools yielding rapid, real-time assessment of data provide a number of potential advantages. The benefits of the MECH-SSDA tool presented here is at least three-fold. First, since automated serial sectioning systems, by design, operate unattended for a significant portion of time, the tracked data help to provide the user a detailed picture of system operation while unattended. Such data can assist in rapid identification of any abnormalities should an unintended event occur during user absence. Second, the tracked data provide the user an empirical method to more reliably and more readily forecast operation time toward experiment completion. With little additional effort, this forecasting can be extended to consumables used (e.g., SiC paper, diamond suspension, abrasive extender, etc.), computer memory to be occupied by the dataset, as well as operational ratios for system usage versus periods of non-use. Lastly, this real-time data collection footprint is useful toward enabling the more ambitious goal of meaningful and robust closed-loop operation.

Closed-loop control in automated serial sectioning systems would provide for intelligent correction of the system without user intervention. However, for this to be possible, real-time assessment of data acquisition compared to some standard would certainly be required. As such, the MECH-SSDA tool, and others of its kind, can provide a useful initial step toward the eventual development of closed-loop operation in automated serial sectioning systems.

Conclusion

Customizations to assist in the operation of an automated serial sectioning system are described herein. These customizations include a non-contact method to assess material removal rates and a real-time operational data collection analyzer called MECH-SSDA. The non-contact material removal assessment is obtainable over a range of 50 mm with a resolution on the order of microns. The real-time data collection analyzer is both deployable and extensible and has been implemented in conjunction with a Robo-Met.3D®, version 2 automated serial sectioning system. The data analysis tool tracks two separate and independent measures of material removal, polishing times, imaging cycle times, as well as total run times. MECH-SSDA represents a very useful step toward the development of a tractable closed-loop integration-based operation that is based on quantifiable metrics of real-time data collection for automated mechanical serial sectioning systems.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A metallographic system comprising:
   a robotic arm configured to manipulate a sample and to present a first top surface of the sample, wherein the arm further comprises a reference structure configured to provide a reference surface that is generally parallel to the first top surface of the sample, and wherein the reference structure and the sample are disposed on a distal portion of the arm;
   a sensor configured to measure a reference distance between the sensor and a portion of the reference surface and to measure a sample distance between the sensor and a portion of the first top surface of the sample;
   an analyzer configured to examine the first top surface of the sample; and
   a polisher configured to polish the first top surface of the sample to provide a second top surface,
   wherein the robotic arm is configured to move the sample between the sensor, the analyzer, and the polisher.

2. The system of claim 1, wherein the reference structure comprises a machined ring disposed on a distal portion of the arm, and wherein the ring is in proximity to the sample that is also disposed on a distal portion of the arm.

3. The system of claim 1, wherein the reference distance is unchanging.

4. The system of claim 1, wherein the sensor is further configured to measure a further sample distance between the sensor and a portion of the second top surface provided by the polisher.

5. The system of claim 1, wherein the sensor comprises:
   a mount; and
   a laser interferometer disposed upon the mount, wherein a laser beam emitted by the interferometer is configured to provide the reference distance and the sample distance.

6. The system of claim 5, wherein the mount comprises a three-axis mount.

7. The system of claim 6, wherein the laser interferometer comprises a red semiconductor laser configured to emit the laser beam.

8. The system of claim 1, wherein the analyzer comprises an optical microscope, an electron microscope, an optical camera, a CCD camera, an X-ray camera, and/or a spectroscope.

9. The system of claim 1, wherein the polisher comprises one or more platens configured to polish a surface of the sample, thereby providing a surface for examination by the analyzer.

10. The system of claim 9, further comprising:
    a loader configured to contain one or more samples; and/or
    a mounting clip configured to mount one or more samples.

11. The system of claim 10, further comprising:
    a processing unit configured to control the robotic arm, the sensor, the analyzer, the polisher, the loader, and/or the mounting clip.

12. The system of claim 11, wherein the processing unit is configured to provide a predetermined degree of polishing by the polisher and configured to measure the reference distance and the sample distance by the sensor.

13. The system of claim 12, wherein the processing unit is further configured to perform image analysis and to position the sample for examination by the analyzer based on feedback from the sensor.

14. The system of claim 11, wherein the processing unit is configured to control the robotic arm to manipulate the sample between the sensor and the analyzer.

15. The system of claim 11, wherein the processing unit is configured to control the robotic arm to manipulate the sample between the polisher and the sensor.

16. The system of claim 11, wherein the processing unit is configured to control the robotic arm to manipulate the sample between the analyzer and the polisher.

17. A method comprising:
    providing a robotic arm configured to manipulate a sample and to present a first top surface of the sample, wherein the arm further comprises a reference structure configured to provide a reference surface that is generally parallel to the first top surface of the sample, and wherein the reference structure and the sample are disposed on a distal portion of the arm;
    manipulating the sample to a sensor, wherein the sensor is configured to measure a first reference distance between the sensor and a portion of the reference surface and to measure a first sample distance between the sensor and a portion of a first top surface of the sample;

obtaining the first reference distance and the first sample distance;

manipulating the sample to an analyzer configured to examine the first top surface of the sample; and examining the first top surface of the sample.

18. The method of claim 17, further comprising, prior to manipulating a sample to a sensor:

manipulating the sample to a polisher configured to polish a surface of the sample to provide the first top surface; and polishing the sample to provide the first top surface.

19. The method of claim 17, further comprising, after examining the first surface:

manipulating the sample to a polisher configured to polish the first top surface of the sample to provide a second top surface; and polishing the sample to provide the second top surface.

20. The method of claim 19, further comprising, after polishing the sample:

manipulating the sample to the sensor, wherein the sensor is configured to measure a second reference distance between the sensor and a portion of the reference surface and to measure a second sample distance between the sensor and a portion of the second top surface of the sample;

obtaining the second reference distance and the second sample distance;

manipulating the sample to the analyzer configured to examine the second top surface of the sample; and examining the second top surface of the sample.

21. The method of claim 17, wherein the reference structure comprises a machined ring disposed on a distal portion of the robotic arm, and wherein the ring is in proximity to the sample that is also disposed on a distal portion of the arm.

22. The method of claim 17, wherein the obtaining step comprises determining the difference between the first reference distance and the first sample distance, thereby establishing a first slice thickness.

23. The method of claim 17, further comprising:

obtaining the sample from a loader configured to contain one or more samples;

washing, rinsing, treating, and/or drying one or more samples; and/or affixing one or more samples onto a handling mount.

* * * * *